(12) United States Patent
Wood (10) Patent No.: US 7,122,033 B2
(45) Date of Patent: Oct. 17, 2006

(54) ENDOLUMINAL RADIOFREQUENCY CAUTERIZATION SYSTEM

(75) Inventor: Bradford J. Wood, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 152 days.

(21) Appl. No.: 10/733,225

(22) Filed: Dec. 10, 2003

(65) Prior Publication Data

US 2004/0122421 A1     Jun. 24, 2004

Related U.S. Application Data

(62) Division of application No. 10/017,619, filed on Dec. 6, 2001, now Pat. No. 6,676,657.

(60) Provisional application No. 60/254,348, filed on Dec. 7, 2000.

(51) Int. Cl.
*A61B 18/18* (2006.01)

(52) U.S. Cl. .................................. 606/41

(58) Field of Classification Search ............ 606/27–52
See application file for complete search history.

(56) References Cited

U.S. PATENT DOCUMENTS

| | | | |
|---|---|---|---|
| 4,522,205 A | 6/1985 | Taylor et al. | |
| 4,655,771 A | 4/1987 | Wallsten | |
| 4,733,665 A | 3/1988 | Palmaz | |
| 4,739,768 A | 4/1988 | Engelson | |
| 4,994,069 A | 2/1991 | Ritchart et al. | |
| 5,041,126 A | 8/1991 | Gianturco | |
| 5,122,136 A | 6/1992 | Guglielmi et al. | |
| 5,222,938 A | 6/1993 | Behl | |
| 5,354,295 A | 10/1994 | Guglielmi et al. | |
| 5,437,664 A | 8/1995 | Cohen et al. | |
| 5,545,193 A * | 8/1996 | Fleischman et al. | .......... 607/99 |
| 5,556,396 A | 9/1996 | Cohen et al. | |
| 5,683,384 A | 11/1997 | Gough et al. | |
| 5,725,547 A | 3/1998 | Chuter | |
| 5,743,905 A | 4/1998 | Eder et al. | |
| 5,851,206 A | 12/1998 | Guglielmi et al. | |
| 5,980,563 A | 11/1999 | Tu et al. | |
| 6,014,589 A | 1/2000 | Farley et al. | |
| 6,024,742 A | 2/2000 | Tu et al. | |
| 6,036,687 A | 3/2000 | Laufer et al. | |
| 6,036,689 A * | 3/2000 | Tu et al. | ....................... 606/41 |
| 6,120,499 A | 9/2000 | Dickens et al. | |
| 6,352,534 B1 | 3/2002 | Paddock et al. | |
| 6,475,213 B1 | 11/2002 | Whayne et al. | |

(Continued)

OTHER PUBLICATIONS

Eskridge et al., "Endovascular Embolization of 150 Basilar Tip Aneurysms with Guglielmi Detachable Coils: Results of the Food and Drug Administration Multicenter Clinical Trials," *Neurosurg Focus*, vol. 5(4): Article 1, 1998.

(Continued)

*Primary Examiner*—Roy D. Gibson
*Assistant Examiner*—Pete Vrettakos
(74) *Attorney, Agent, or Firm*—Klarquist Sparkman, LLP (57) ABSTRACT

Disclosed are methods and devices for occluding the lumen of a hollow organ by delivering radiofrequency energy to the inner wall of a hollow organ. The disclosure includes radiofrequency electrodes that expand, in a deployed condition, to contact the walls of the organ. In some embodiments, the electrodes substantially conform to the inner wall to enhance therapeutic contact. Methods are also disclosed for using these electrodes to totally or partially occlude a lumen, or remove or reduce a total or partial occlusion of a lumen.

27 Claims, 4 Drawing Sheets

U.S. PATENT DOCUMENTS 6,488,680 B1 12/2002 Francischelli et al.
2002/0111548 A1* 8/2002 Swanson et al. ............ 600/407

OTHER PUBLICATIONS

Shireman et al., "Treatment of Venous Malformations by Direct Injection with Ethanol," *J. Vasc. Surg*, vol. 26(5): pp. 838-844, Nov. 1997.

Sivak and Catalano, "Endoscopic Ligation of Esophageal Varices," *Ann. Intern. Med*, vol. 119(1): pp. 87-88, Jul. 1993.

Takebayashi et al., "Transarterial Embolization and Ablation of Renal Arteriovenous Malformations: Efficacy and Damages in 30 Patients with Long-Term Followup," *J. Urol.*, vol. 159(3): pp. 696-701, Mar. 1998.

* cited by examiner

ENDOLUMINAL RADIOFREQUENCY CAUTERIZATION SYSTEM

CROSS REFERENCE TO RELATED APPLICATIONS

This application is a Divisional of Ser. No. 10/017,619 filed on Dec. 6, 2001 now U.S. Pat. No. 6,676,657 which claims benefit of 60/254,348 Dec. 7, 2000.

FIELD

The invention relates to methods and devices for occluding hollow organs in a subject, for example by inducing thrombotic, vasospastic and/or fibrotic occlusion of blood vessels. The invention also relates to methods and devices for increasing the lumen diameter of hollow organs.

BACKGROUND

It is sometimes therapeutically desirable to occlude blood flow in one or more blood vessels of a human or animal subject. This circumstance may arise in a variety of clinical conditions, such as an acute bleeding episode. Such bleeding may occur from any organ after trauma, or may result from a variety of pathologic conditions such as ulcers, tumors, diverticulitis, portal hypertension, or postpartum hemorrhage.

In many such situations, an invasive surgical approach may be attempted. For example, after pelvic or abdominal trauma, a surgeon may perform open or laparoscopic surgery. The source or sources of bleeding may be identified, cauterized or ligated. However, surgical procedures carry substantial morbidity and mortality rates. There is often an emergent need to control bleeding in order to save the life of the subject, and the subject may expire during the time needed to prepare an operating suite, induce anesthesia, and perform the procedure. In addition, open surgery adds substantial additional stress for the subject.

Accordingly, health care practitioners have sought a more rapid and/or less invasive means of controlling bleeding. For example, a practitioner may access the interior of the subject's blood vessels by inserting a catheter via a percutaneous approach. A variety of sclerosing or embolic agents may be injected through the catheter, such as ethanol, microfibrillar collagen, Gelfoam, silastic beads, polyvinyl alcohol foam, or polymer resins. The use of some of these agents are described in U.S. Pat. Nos. 5,580,568; 5,667,767; and 6,059,766; Vedantham, et al., Am. J. Obstet. Gynecol. 176: 938–948, 1997; and Imembo, Diverticular Disease of the Colon, Sabiston: Textbook of Surgery, 15th ed., page 987, © 1997 W.B. Saunders Company. Other percutaneous alternatives include blood coagulation by endovascular delivery of local heat, either by laser or an electrical heating coil, for example, as described in U.S. Pat. Nos. 4,735,201 and 5,851,206.

In addition to control of bleeding, it also may be therapeutically desirable to induce thrombosis in pathologic vascular conditions such as aneurysms, arteriovenous malformations, and arteriovenous shunts, for example as described in U.S. Pat. Nos. 5,122,136; 5,354,295; and 5,894,022; O'Reilly et al., Radiology 171: 471–474, 1989; Kinugasa et al, J. Neurosurg. 77: 501–507, 1992; Taki et al., J. Neurosurg. 77: 37–42 1992; and Takebayashi et al., J. Urol. 159: 696–701, 1998. Blood vessels supplying a tumor represent another target for therapeutic thrombosis; see, for example, U.S. Pat. Nos. 6,093,399 and 6,015,541; and Castaneda-Zuniga, et al., Vascular Embolotherapy, in Interventional Radiology, Part 1, 1: 9–32, Williams & Wilkins, 1992. Such thrombosis may limit tumor growth or metastatic potential by reducing its blood supply.

In addition to blood vessels, it may also be therapeutically desirable to occlude the lumen of other hollow organs. For example, ligation or occlusion of the fallopian tubes of a female subject or the vas deferens of a male subject may provide effective contraception.

Radiofrequency energy has been used to occlude blood vessels, as described in U.S. Pat. No. 5,743,905; to treat vascular aneurysms, as described in U.S. Pat. No. 5,122,136, and to occlude other hollow organs such as fallopian tubes, as described in U.S. Pat. No. 5,556,396. However, energy delivery to the inner wall of the vessel may be imprecise, due to a failure of the electrode to conform optimally to the inner wall. Much of the electrode may not be in contact with the inner wall, but instead remains in the lumen. Instead of being delivered to the vascular wall, energy is dissipated into the blood stream. Thus, the vascular tissue may be incompletely cauterized, or alternatively, may be perforated by excessive energy delivery at an isolated contact point.

In addition to occluding lumens of hollow organs, under some clinical circumstances it may be therapeutically desirable to increase lumen diameter. For example, it may be desirable to reduce a stricture or stenosis in a bronchus, esophagus, a segment of intestine, or a blood vessel. In arteries, it may be desirable to reduce a stenosis that reduces blood supply to an organ, for example, a stenosis in a coronary artery that reduces blood supply to the working heart muscle. Moreover, it may be desirable to reduce a restenotic lesion, that is, a stricture or stenosis in a hollow organ that has recurred at least once after a procedure that reduced the severity of the stricture or stenosis. For example, an artery may develop a restenotic lesion after a successful angioplasty procedure at the site of an atherosclerotic stenosis. Such restenotic lesions may develop even when a stent is placed after angioplasty to prop open the vessel. When arterial restenosis occurs after stent placement, it is referred to as in-stent restenosis. Current therapeutic options for in-stent restenosis are limited, and surgery is often required.

SUMMARY

Disclosed herein are several specific examples of a device for delivering electrical energy, such as radiofrequency energy, to the walls of a body lumen using a nonconductive catheter. A conductive member capable of conducting an electrical signal is contained within the catheter, and the conductive member is movable between a non-deployed position within the catheter, and a deployed position in which the conductive member is advanced longitudinally through and out of the catheter, wherein the conductive member conforms to the walls of the lumen when the conductive member is in the deployed position.

In some examples, the conductive member in the non-deployed position slides within the catheter, but in the deployed position it assumes a preformed envelope external to the catheter in which the envelope tapers towards both its ends. In particular examples, the catheter in the non-deployed position is linear and non-helical, but in the deployed position is a helix. The helix has an enlarged central diameter that is greater than a proximal diameter of the helix where it emerges from the catheter, and is greater than a distal diameter of the helix at a distal end of the conductive member. In some embodiments, the catheter has a side port through which the conductive member is advanced, which is particularly helpful when the catheter is being introduced into some aneurysms that evaginate from the wall of the blood vessel.

Some of the disclosed examples have an expandable distal end that is retracted, or collapsed into a compact configuration, in the non-deployed position and is expanded in the deployed position. The expandable distal end can assume the form of a plurality of struts that extend longitudinally with respect to the conductive member, and the struts are attached to the conductive member such that longitudinal movement of the conductive member moves the struts between the retracted and expanded positions. For example, the struts are attached at a first end to the conductive member and are fixed at a second end around the conductive member, such that longitudinal movement of the conductive member (for example retraction of the conductive member toward the sheath) forces the struts into the expanded position. The device can include a sheath around the catheter, to which the proximal end of the struts is attached. Then as the distal end of the conductive member is pulled toward the sheath, the struts are compressed and expand to the deployed position in contact with the wall of the lumen.

Some embodiments of the device also include an expandable cuff around the catheter proximal to the expandable member when the expandable member is in the deployed position. Alternatively, expandable cuffs can be provided both distal and proximal to the expandable member, to effectively isolate the expandable member when the electrical energy is supplied to the wall of the lumen (for example, when the device is used to open a vascular occlusion, as in a coronary artery).

In yet another example of the device, the conductive member is an electrically conductive biocompatible liquid, for example a hypertonic liquid, such as hypertonic saline. The catheter is provided with a plurality of ports through which the liquid is deployed to contact the wall of the lumen. When the ports are arranged peripherally around the catheter near the distal tip of the catheter, pressurized expulsion of the conductive liquid can occur as an electrical current is applied through the liquid to the wall of the lumen. The device can further include a source of the biocompatible conductive liquid in communication with the catheter, a pressure source capable of selectively moving the liquid through the catheter, and a source of electrical energy (such as radiofrequency energy) selectively in contact with the liquid.

In other particular non-limiting examples, the device is a nonconductive flexible catheter for introduction into the lumen of a blood vessel, wherein the catheter has a side port in the catheter wall. A conductive wire extends through the catheter, and is made of a memory material such that the wire is non-helical when the conductive wire is in the catheter, but it assumes a helical shape when the wire is advanced out of the catheter through the side port. The wire conforms to the walls of the lumen when the conductive member is in the deployed position, for example assuming an envelope (circumscribing the overall shape of the deployed wire) that tapers toward both ends of the helix, to help conform, for example, to a shape of an aneurysm. The wire can be selectively connected to a source of energy (such as radiofrequency energy) to deliver a signal of a pre-selected intensity for a pre-selected period of time to occlude the aneurysm.

In another particular non-limiting example, a device for delivering electrical energy to a wall of a body lumen includes a non-conductive catheter for introduction into a body lumen, and a conductive wire that extends through the catheter. The wire has a proximal portion that can slide through the catheter for advancing the wire through the catheter, and a distal portion which has a radially expandable member that contacts the wall of the lumen. The expandable member may be, for example, a plurality of longitudinally extending struts that are located at the distal portion of the wire. The struts are radially expanded by longitudinal movement of the wire, with the expandable member in the retracted position, until the expandable member emerges from the catheter. Once the expandable member has emerged from the catheter, it can selectively be expanded in position so that the struts contact the wall of the lumen. In certain embodiments, the expandable member can include longitudinally adjacent first and second (or more) expandable members.

The struts may be arranged to extend longitudinally along the conductive wire, with a first end attached to the conductive wire and a second end attached to a fixation member that is selectively movable relative to the wire. Relative movement between the conductive wire and fixation member retracts and expands the struts. For example, the fixation member may be a sheath or ring around the conductive wire, and the second ends of the struts are attached to the sheath or ring. When the distal ends of the struts are attached to the movable wire, slight retraction of the wire into the catheter through the sheath or ring forces portions of the struts intermediate their opposite ends outwardly away from the longitudinal axis of the wire. The catheter can be a blood vessel catheter, and the struts are expanded once the catheter has been introduced into the blood vessel.

In another specific non-limiting example of a device for delivering electrical energy to a wall of a body lumen, the catheter includes a plurality of fluid orifices that communicate with a catheter lumen. A source of biocompatible conductive liquid selectively communicates with the catheter lumen, and a pressure source selectively moves the conductive liquid though the catheter lumen and out of the fluid orifices into contact with the wall of the body lumen. A source of electrical energy selectively energizes the liquid in the catheter to conduct electrical energy through the liquid as it is moved out of the fluid orifices. The liquid conforms to the walls of the lumen as it is propelled under pressure from the catheter, to precisely deliver the electrical energy to the lumen wall.

The disclosed embodiments also include a method of applying electrical energy to a wall of a body lumen, by introducing a non-conductive catheter into the body lumen, such as a blood vessel (including an aneurysm) or hollow viscus (such as the esophagus). A conductive member is advanced longitudinally through the catheter until it emerges from the catheter, and assumes a shape that contacts the walls of the body lumen. For example, the conductive member is non-helical inside the catheter, but it is made of a memory material that assumes a helical shape after it emerges from the catheter. The helix has an envelope (outline) that tapers toward both its ends, from a relatively enlarged center diameter. In particular embodiments, the conductive member is advanced out of the catheter through a side port in the catheter, and the lumen is an aneurysm lumen. Electrical energy is supplied to the conductive member to, in turn, apply the electrical energy (such as radiofrequency energy) to the wall of the body lumen, which can obliterate the lumen (for example, to treat an aneurysm).

In yet other embodiments of the method, the conductive member includes a distal portion (such as a plurality of longitudinally extending struts) that expands to contact the wall of the lumen. In a retracted position the struts slide through the catheter, but in the expanded position they contact the wall of the lumen. The struts are moved between the retracted and expanded position by longitudinal movement of the conductive member through the catheter.

In other embodiments of the method, the conductive member is a biocompatible conductive liquid that is forced out of the catheter into contact with the walls of the body lumen, as electrical energy is supplied to the liquid, to deliver the energy (such as radiofrequency energy) to the wall of the lumen.

DETAILED DESCRIPTION

As used herein, "proximal" refers to a portion of an instrument closer to an operator, while "distal" refers to a portion of the instrument farther away from the operator.

As used herein, the term "comprises" means "includes."

As used herein, the singular forms "a," "an," and "the" include plural referents unless the context clearly dictates otherwise. For example, the term "a wire" includes one or more wires and can be considered equivalent to the term "at least one wire."

This detailed description discloses several devices for delivering energy, such as radiofrequency energy, to the lumens of hollow organs, for example to partially or completely occlude such lumens or remove partial or complete occlusions from the lumens. These disclosed devices have expandable portions that conform to the inner walls of the hollow organ, to improve energy transfer and assure more uniform and complete delivery of energy to the inner walls.

One such device disclosed herein delivers radiofrequency energy to a hollow organ of a subject. The device includes a substantially tubular catheter having proximal and distal openings that is constructed from a nonconductive material. The catheter substantially surrounds an electrode, except for the proximal portion of the electrode that is accessible through the proximal catheter opening. The electrode is deployed in the lumen of a hollow organ through the distal catheter opening. Upon deployment, the distal electrode end substantially conforms to an inner surface of the hollow organ, and a therapeutically effective amount of RF energy is delivered through the electrode, such that the lumen is substantially occluded.

The distal catheter opening in this embodiment may have at least one side hole and/or end hole. In some embodiments, the electrode is constructed from a material having a memory function, for example titanium-nickel alloys such as Nitinol™. In specific embodiments, the electrode has an outer coating that reduces adherence of the electrode to the organ, and/or is constructed so that the distal electrode end detaches upon delivery of a therapeutically effective amount of RF energy to the electrode. In other embodiments, the electrode is a biocompatible liquid, such as hypertonic saline, or is made from a biodegradable material, such as ionic collagen.

In other specific embodiments, the electrode has two or more substantially coaxial sections, each of which may be advanced, retracted, or rotated independently of the other. This embodiment may have one coaxial section substantially surrounding the second coaxial section. The first coaxial section is then a circumferential electrode section, and the second coaxial section is a movable core, that is, a central section of the electrode that is movable independently of the circumferential electrode section. Moreover, the electrode may have two or more movable cores.

In still other specific embodiments, the distal electrode end may be constructed so that one or more electrode sections are attached to the movable core at a distal approximation area, and are attached to the circumferential electrode section at a proximal approximation point. Upon deployment, the central electrode area between the proximal and distal approximation points substantially conforms to the inner surface of the organ. Moreover, in specific embodiments, the size or shape of the central area is modifiable, for example, by rotating, advancing, or retracting the movable core relative to the circumferential electrode section.

The radiofrequency energy delivered to the electrode has a frequency of about 5 kHz to about 1 GHz. In specific embodiments, the RF energy may have a frequency of about 10 kHz to about 1000 MHz; or about 10 kHz to about 10 MHz; or about 50 kHz to about 1 MHz.

In other specific embodiments, the device may have a thermistor that measures temperature in the lumen, and a thermistor may be a component of a microprocessor-controlled system that receives temperature information from the thermistor and adjusts wattage, frequency, duration of energy delivery, or total energy delivered to the electrode.

In yet other specific embodiments, the device may have temporary lumen occluders that may be proximal or distal to the deployed distal electrode.

Also disclosed are methods for substantially occluding a lumen, such as the lumen of a hollow organ, in a subject by deploying any of the above-described device embodiments in the lumen. For example, specific disclosed methods include: deploying electrodes of material having a memory function, such as Nitinol™; deploying electrodes having biodegradable material or an outer coating; deploying electrodes having a biocompatible liquid, such as hypertonic saline; deploying electrodes having a detachable distal end; deploying electrodes having two substantially coaxial sections that are independently movable relative to each other, such as movable cores; or deploying electrodes in which the size or shape of the distal electrode's center section is modifiable by altering the position of the movable core relative to the circumferential electrode section. Once any of these various electrode embodiments are deployed, a therapeutically effective amount of RF energy is delivered through the electrodes, such that the lumen is substantially occluded.

In the disclosed methods, about 1 watt to about 500 watts are delivered to the electrode, for about one second to about 200 seconds. In specific embodiments, about five watts to about 200 watts are delivered for about one second to about 200 seconds; or about five watts to about 200 watts are delivered to the electrode for about two seconds to about 60 seconds; or about 20 watts to about 200 watts are delivered to the electrode for about two seconds to about 60 seconds; or about 20 watts to about 200 watts are delivered to the electrode for about five seconds to about 60 seconds.

In specific embodiments, the method is a method of controlling bleeding, ablating an arteriovenous malformation, repairing a vascular aneurysm, or reducing blood supply to a tumor. In other specific embodiments, the method is a method of ablating a venous malformation known as a varix, for example, an esophageal varix.

In other specific embodiments, the method may be a method for increasing the diameter of a hollow organ lumen within a subject by deploying in the lumen any of the disclosed devices and delivering a therapeutically effective amount of RF energy to the electrodes, such that the lumen diameter is increased. In specific embodiments, the hollow organ is an artery, for example an artery with a stenosis or an artery with a restenotic lesion, such as in-stent restenosis.

Figure 1:
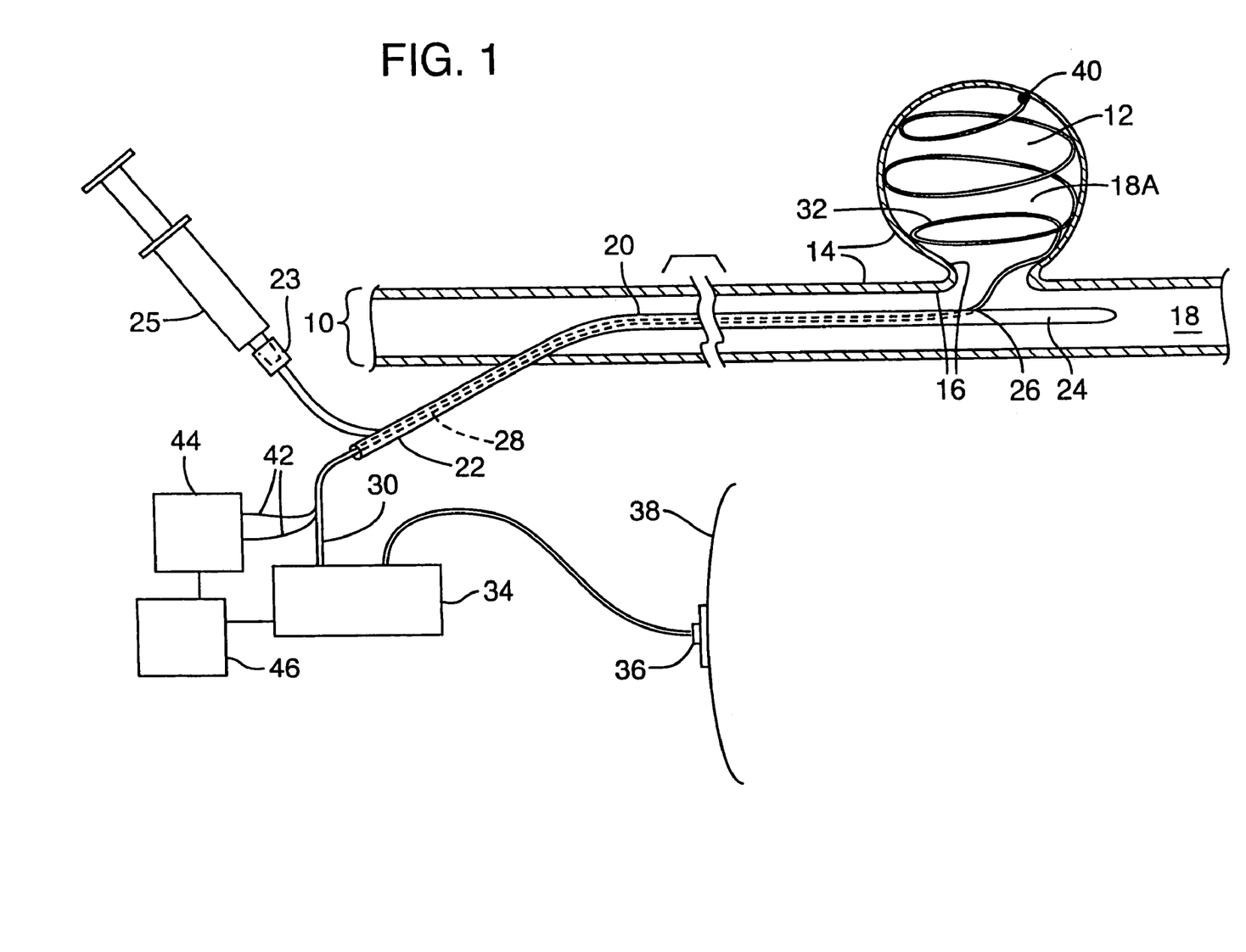
FIG. 1 illustrates an embodiment of a device for altering lumen size in a hollow organ, showing the device with a monopolar electrode deployed in a vascular aneurysm.

Referring now to the drawings, FIG. 1 illustrates one embodiment of a device for substantially occluding the lumen of a hollow organ, showing the device inserted in an artery 10, and deployed in a vascular aneurysm 12. Artery 10 is substantially tubular and has an outer surface 14, which is continuous with outer surface 14 of aneurysm 12. Artery 10 and aneurysm 12 also share a substantially continuous inner surface 16. Inner surface 16 surrounds the arterial lumen 18, which is continuous with the interior 18A of aneurysm 12.

A substantially tubular, hollow catheter 20 is positioned in the arterial lumen 18. Catheter 20 has a proximal end 22, a distal end 24, and side hole 26. An injection port 23 communicates with hollow interior of catheter 20, and may receive a syringe 25 or the like for injection of liquid into the catheter.

Catheter 20 surrounds electrode 28, except at a proximal electrode end 30. A distal electrode portion 32 is illustrated in the deployed state, that is, having been advanced through catheter 20 out catheter side hole 26 and deployed into the cavity of aneurysm 12. Distal electrode portion 32 substantially conforms to inner surface 16 of aneurysm 12. In the non-deployed state (not shown), distal electrode portion 32 is held within and substantially surrounded by catheter 20, and is not advanced through side hole 26.

Proximal electrode end 30 is attached to a radiofrequency generator 34. RF generator 34 may be grounded by attaching a ground 36 to a subject's skin 38; alternatively, electrode 28 may be arranged in a bipolar configuration (not shown). A sensor 40 near distal electrode end 32 is connected via leads 42 to a temperature monitor 44. Temperature monitor 44 is operably connected to a microprocessor 46, and microprocessor 46 is operably connected to RF generator 34. Several other configurations are possible for controlling RF output to the electrode, such as those described in U.S. Pat. Nos. 6,080,149; 5,935,123; 5,556,396; 5,514,129; 5,496,312; 5,437,664; and 5,370,645.

Catheter 20 is constructed of an insulative material, such as a material having a resistance of about 500 kilohms per cm or greater. Examples of suitable materials include silicon tubing, polypropylene, high-density polyethylene, or low-density polyethylene. Catheter diameter may vary with a particular embodiment. For example, in vascular applications such as arterial occlusion, suitable catheter diameters may vary from about 1 French (0.33 mm) to about 24 French, or from about 3 French through about 12 French. For ablation of smaller arterioles or veins, or cerebral aneurysms, microcatheters may be appropriate. Such microcatheters have a wall thickness of about 0.001 to about 0.005 inches, and an inner diameter of about 0.005 to about 0.1 inches. Examples of microcatheters are described in U.S. Pat. Nos. 4,884,579 and 4,739,768.

Electrode 28 may be constructed of any suitable conductive material. Examples include stainless steel and platinum alloys. Electrodes also may be constructed from memory metal alloys, as described in U.S. Pat. Nos. 5,935,123 and 6,071,280, for example titanium-nickel alloys such as Nitinol™. Additional examples are described in K. Shimizu and T. Tadaki, Shape Memory Alloys, H. Funakubo, Ed., Gordon and Breach Science Publishers, 1987. Preformed electrodes are described in U.S. Pat. Nos. 5,827,276 and 5,855,576. In most instances, these alloys demonstrate the ability to return to a previously defined shape or size when heated. Generally, these materials can be plastically deformed at a relatively low temperature, for example, below about 15° C. Upon exposure at a higher temperature, for example about 25° C. to about 45° C., they return to their shape prior to the deformation. See M. Simon, et al., Radiology 172: 99–103, 1989, which discloses the use of such alloys to construct a venous filter device.

Electrodes may be preformed to particular advantageous shapes, such as a spiral configuration illustrated in FIG. 1, basket configurations, and the like.

In the deployed state illustrated in FIG. 1 the electrode, or conductive member, extends outwardly through a side port in the catheter and laterally of the catheter. The conductor member expands to, or assumes, the position, or configuration, of a helix having an enlarged central diameter positioned in the mid-region of aneurysm 12. The central diameter of the helix shown in FIG. 1 is greater than both the proximal diameter of the helix adjacent the catheter and the distal diameter of the helix at the distal end of the conductive member.

When memory metal alloys are used to construct preformed electrodes, they may be prevented from assuming their preformed configuration prior to deployment, by perfusing with chilled solutions (cooled to between about 0° C. and 15° C.), such as chilled saline. These chilled solutions may be infused through injection port 23. Upon deployment, the electrode warms and assumes its preformed shape, for example, the spiral configuration illustrated in FIG. 1 or the basket configurations illustrated in FIGS. 2A, 2B, and 2C.

Electrodes also may be constructed from biodegradable material such as ionic collagen, cross-linked collagen-mucopolysaccharide composites, and the like; see, for example, U.S. Pat. No. 4,280,954. In addition, electrodes may be partially or fully coated with an insulative material, generally having a resistance of about 500 kilohms per cm or greater. Such material may be selected to reduce tissue adhesion during operation. A variety of polymers are appropriate for these purposes, such as polyethylene, polypropylene, polyurethane, polyvinyl chloride and the like. Biodegradable materials are also suitable as coating for electrodes, for example, pectin, agar, arabic gum, xanthum gum, tragacanth gum, starches, celluloses, polyvinyl alcohol, polyvinylpyrrolidone, and the like.

The electrode may be a biocompatible liquid. A biocompatible liquid is a material that is liquid at body temperature, and does not itself cause a clinically evident illness or injury in the subject, other than occlusion of the hollow organ being treated, when given to the subject in quantity necessary to serve as a conductor of a therapeutic amount of energy. Biocompatible liquids capable of conducting RF energy include hypertonic liquids such as hypertonic saline, and are suitable for use as RF electrodes.

Catheter 20 or electrode 28 may be constructed with markers that assist the operator in obtaining a desired placement, such as radioopaque markers, etchings, or microgrooves. Thus, catheter and electrode may be constructed to enhance their imageability by techniques such as ultrasounds, CAT scan, or MRI. In addition, radiographic contrast material may be injected through hollow interior of catheter 20 through injection port 23, thereby enabling localization by fluoroscopy or angiography.

In operation, catheter 20 is inserted into lumen 18 through outer surface 14 and inner surface 16 of artery 10. Insertion may be percutaneous, such as described in U.S. Pat. Nos. 4,994,069, 4,884,575, and 4,739,768. Alternatively, catheter 20 may be inserted through a surgically created arteriotomy or during an open surgical procedure. Moreover, insertion into nonvascular hollow organs is often possible without penetrating the catheter through the surface of the organ. For example, an esophagus or bronchi is readily accessible through the oral cavity of a subject.

In the non-deployed state (not shown), distal electrode end 32 is substantially surrounded by catheter 20 and has not been advanced through side hole 26 into arterial lumen 18 or aneurysm cavity 12. The electrode is deployed into the lumen or aneurysm cavity as illustrated in FIG. 1, by advancing electrode 28 through catheter side hole 26 so that distal electrode end 32 is substantially in contact with inner surface 16 of aneurysm 12.

After distal electrode end 32 is placed in desired position, radiofrequency energy is applied to electrode 28 and conducted to distal electrode end 32. The RF energy may be delivered at any of a broad range of frequencies, for example about 5 kHz to about 1 GHz; or about 10 kHz to about 1000 MHz; or about 10 kHz to about 10 MHz; or about 50 kHz to about 1 MHz. A range of energy may be delivered to the electrode; for example about 1 watt to about 500 watts, for about one second to about 200 seconds; or about 5 watts to about 200 watts for about one second to about 200 seconds; or about five watts to about 200 watts for about two seconds to about 60 seconds; or about 20 watts to about 200 watts for about two seconds to about 60 seconds; or about 20 watts to about 200 watts for about five seconds to about 60 seconds. Selection of a particular frequency or frequencies, time of energy delivery, total energy delivered, and other parameters may depend upon tissue characteristics, size of lumen, blood flow through the lumen, tissue impedance, and other factors.

Delivery of RF energy may be regulated by monitoring temperature, tissue impedance, or other parameters at or near the site of deployed distal electrode end 32. Sensor 40 receives temperature information and transmits the information to temperature monitor 44 via leads 42. The temperature monitor transmits information to microprocessor 46, which controls output from RF generator 34 based on the temperature information. Suitable thermal sensors include a T-type thermocouple with copper constantene; J-type, E-type, or K-type thermal sensors; thermistors; fiber optics; resistive wires; thermocouple IR detectors; and the like.

Sensor 40 need not be a thermal sensor. Additional or alternative sensors may be present to monitor tissue impedance and relay the information in like manner to microprocessor 46. For example, see U.S. Pat. Nos. 5,556,396 and 5,935,123.

Impedance also may be used to monitor voltage and current. Output from sensor 40 is used by microprocessor 46 to control the delivery of RF energy to the tissue site.

Figures 2A, 2B:
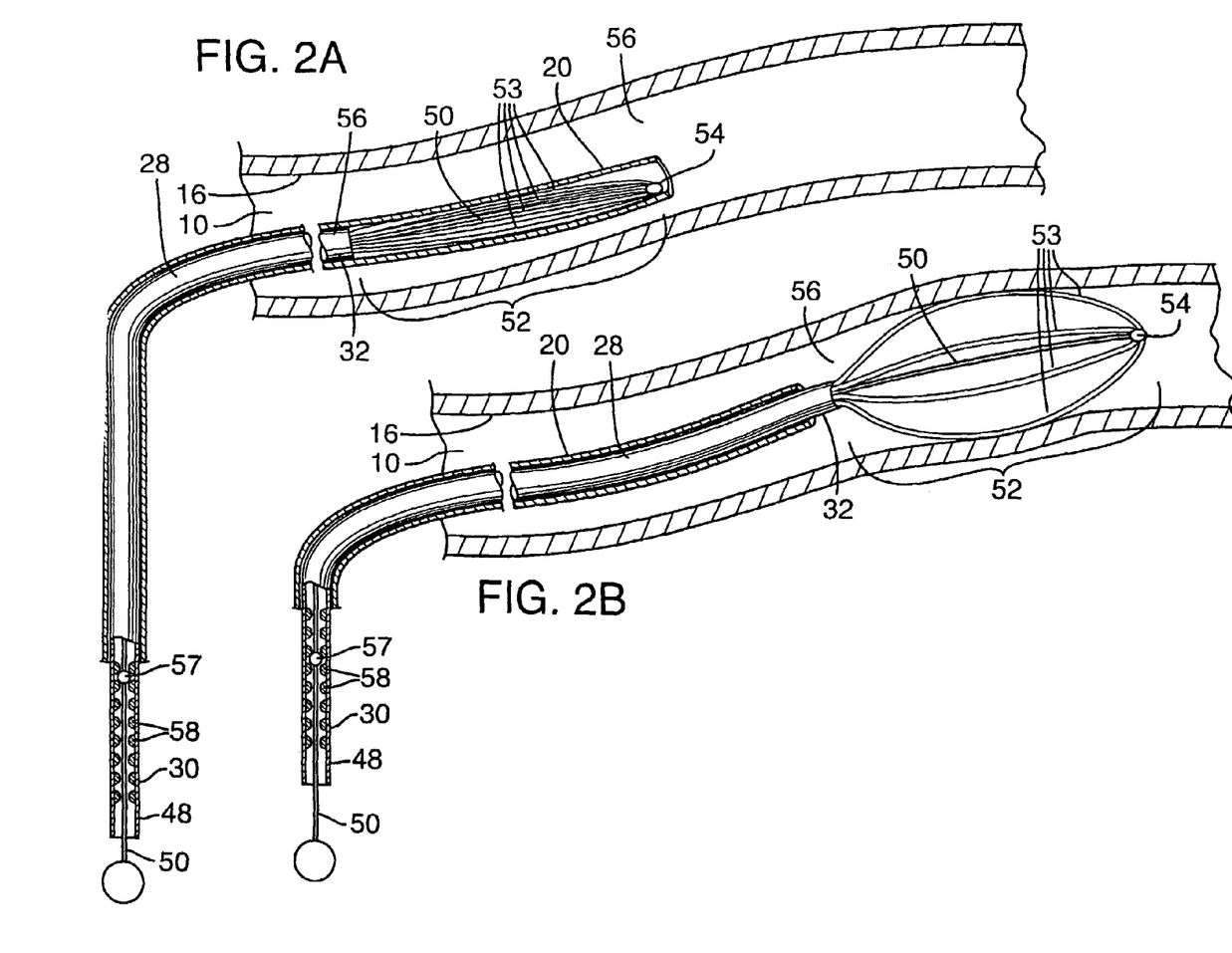
FIGS. 2A, 2B, 2C, and 2D illustrate other embodiments, with FIGS. 2A and 2B showing a basket-type distal electrode with a movable core deployed in a hollow organ in different positions.

FIGS. 2A–D illustrate additional embodiments, in which the electrode is shown in alternative configurations. For example, FIG. 2B illustrates an electrode having multiple components in its deployed state. Catheter 20 substantially surrounds electrode 28, except for proximal electrode end 30 and distal electrode end 32. Electrode 28 is comprised of two substantially coaxial segments, a first coaxial section 48 that substantially surrounds a second coaxial section 50. Second coaxial section 50 is referred to herein as a movable core. Movable core 50 extends more distally than first coaxial section 48. In addition, the two coaxial sections are slidably and rotationally adjustable relative to each other. The distal electrode end is comprised of a central area 52 having plurality of electrodes, or struts 53, that are joined to the movable core 50 at a distal approximation point 54, and to the first coaxial section at a proximal approximation point 56.

The electrodes, or struts 53, of central area 52 are illustrated in a substantially coaxial configuration. However, these electrodes may be non-coaxial, for example in a weave-type configuration similar to that illustrated for the intraluminal stents described in U.S. Pat. No. 4,655,771. Configurations similar to other stents, such as those described in U.S. Pat. Nos. 4,886,062 and 4,733,665 are suitable for use as the distal electrode end, as are self expanding stents, for example as described in U.S. Pat. Nos. 6,033,436; 5,849,037 and 5,799,384.

In operation, the embodiment of FIG. 2A initially is retracted with distal electrode end 32 within catheter 20. In FIG. 2B, this embodiment is shown deployed by advancing distal electrode end 32 out of an end hole or a side hole of catheter 20, resulting in a deployed state as illustrated in FIG. 2B. To properly conform to inner wall 16 of blood vessel 10, the distance between distal approximation point 54 and proximal approximation point 56 is adjusted by slidably moving movable core 50 relative to first coaxial section 48. In general, contact of central area electrodes 53 with vascular wall 16 is increased by reducing the distance between distal approximation point 54 and proximal approximation point 56. This reduction in distance may be accomplished by moving movable core 50 in a proximal direction, or moving first coaxial section 48 in a distal direction.

To assist placement and conformation of the distal electrode end to the inner surface of a blood vessel, a radiographic contrast agent may be injected through the catheter to define the vessel walls, as described for the embodiment of FIG. 1. Any part of the electrode or catheter also may be made radioopaque to assist in proper localization of electrodes. Alternatively, any part of the electrode or catheter may be roughened or notched to assist in ultrasonic localization.

Once a desired size and/or shape of the deployed distal electrode end is obtained, the size and/or shape may be maintained by a ball and detente system or the like. Ball 57 surrounds and is fixed to movable core 50. A series of detentes 58 provides frictional resistance to free motion of movable core 50 relative to first coaxial section 48. This frictional resistance may be overcome by the application of a small amount of force, for example by a modest push, pull, or twist by an operator. In this manner, distal electrode end 32 can be set in a desired configuration, thus allowing subsequent hands-free operation. Alternatives to this ball and detente system for maintaining the size and/or shape of the deployed electrode end are readily available, such as a screw system or a bayonet fitting.

Figure 2C:
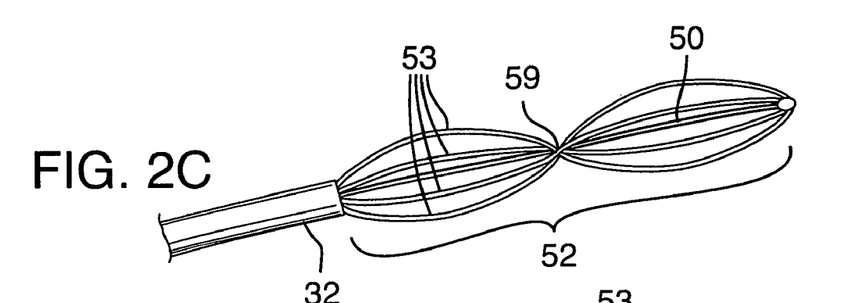

FIG. 2C illustrates the rotation of movable core 50 relative to first coaxial section 48, resulting in a "dual basket" configuration of electrodes in central area 52. An approximately 360 degree rotation of movable core 50 relative to first coaxial section 48 results in a central approximation point 59 at which the plurality of electrodes 53 in central area 52 come into close approximation with each other. It is also possible to construct the central area so that central approximation point 59 is fixed (for example, by a collar surrounding the central approximation point, or by using preformed electrodes made of memory metal alloys, allowing a dual basket configuration without the need to rotate movable core 50. More than two baskets may be present. Short-circuits are prevented by providing the central area electrodes with an insulative coating. Movable core 50 is freely movable through central approximation point 59 and may be rotated, advanced, or retracted to alter the size and shape of the dual basket.

Figure 2D:
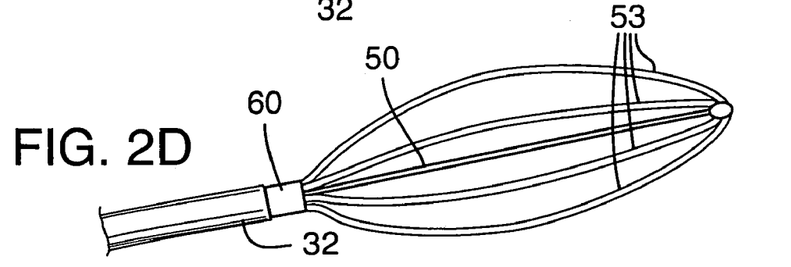

FIG. 2D illustrates an embodiment in which distal electrode 32 is detachable at detachment area 60. This detachment area 60 may be an area of solder or degradable material that melts and detaches when a therapeutically effective amount of radiofrequency energy is delivered to distal electrode end 32. After detachment, distal electrode end 32 may be left in blood vessel as a thrombogenic nidus that enhances occlusion.

Figure 3A:
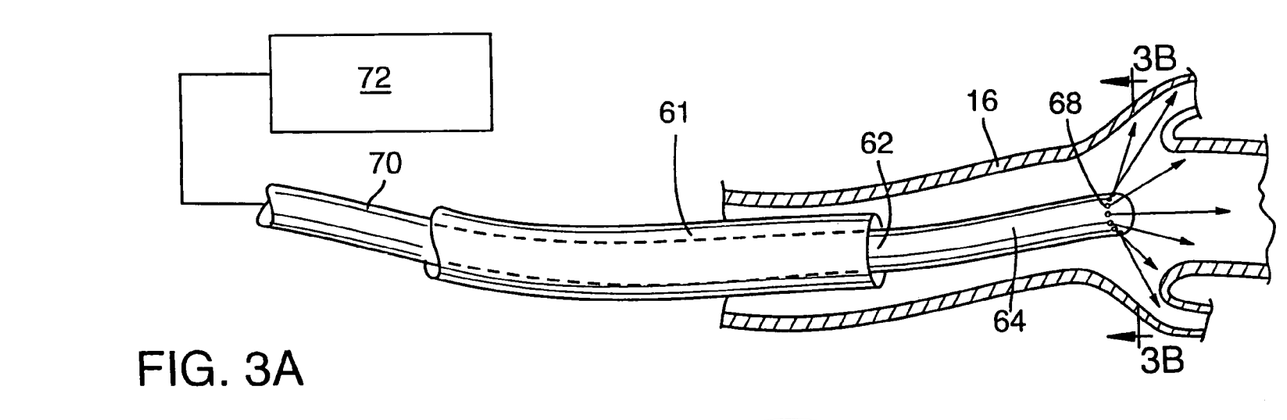
FIG. 3A illustrates a side elevation view of another embodiment of the device, showing the use of biocompatible liquids as conducting electrodes.
Figure 3B:
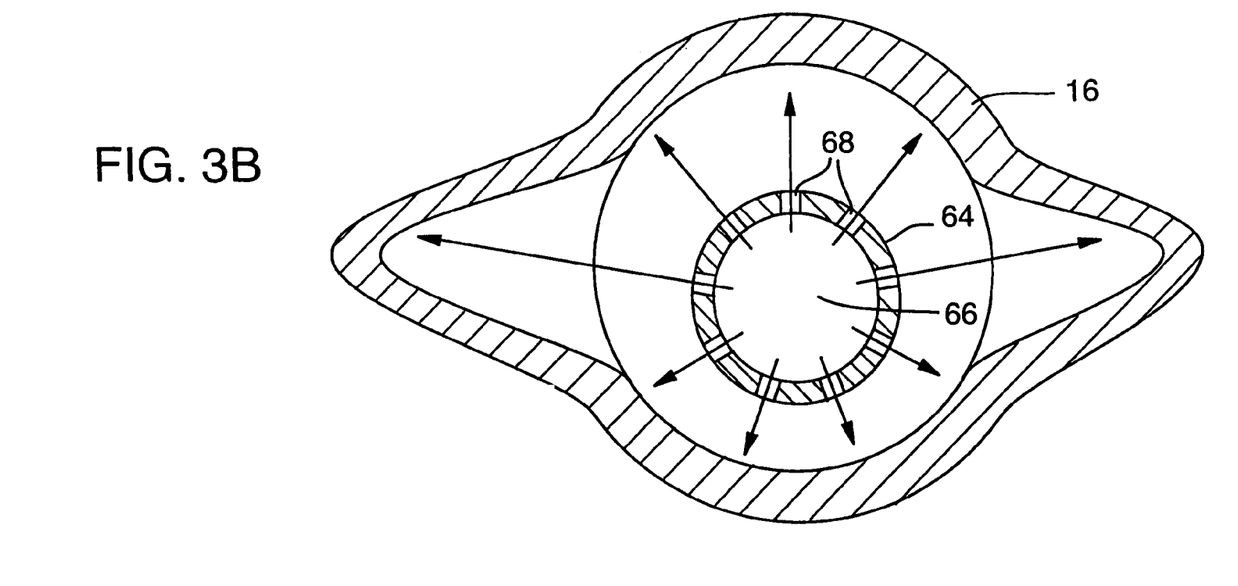
FIG. 3B is an enlarged cross-sectional view taken along the line 3B—3B in FIG. 3A.

FIGS. 3A and 3B illustrate another embodiment in which a biocompatible liquid serves to conduct radiofrequency energy. Catheter 61 surrounds electrode 62, which has a substantially circumferential first coaxial section 64 and a hollow core 66. One or more channels 68 penetrate from hollow core 66 through first coaxial section 64 and communicate with the exterior. Channels may be in a side hole configuration, an end hole configuration, or both. The proximal electrode end 70 is operably connected to a pump 72, or syringe or the like, which can move biocompatible liquid through hollow core 66, through channels 68, to the exterior of the catheter. Proximal electrode end 70 also is connected to a RF energy source (not shown), as was illustrated for proximal electrode end 30 in FIG. 1. As was shown in FIG. 1, proximal electrode end 70 also may be operably connected to a temperature sensor and microprocessor. The embodiment illustrated in FIGS. 3A and 3B may be useful for arteriovenous malformations, where it is sometimes necessary to ablate numerous vascular branches in order to achieve an optimal result.

Figure 4:
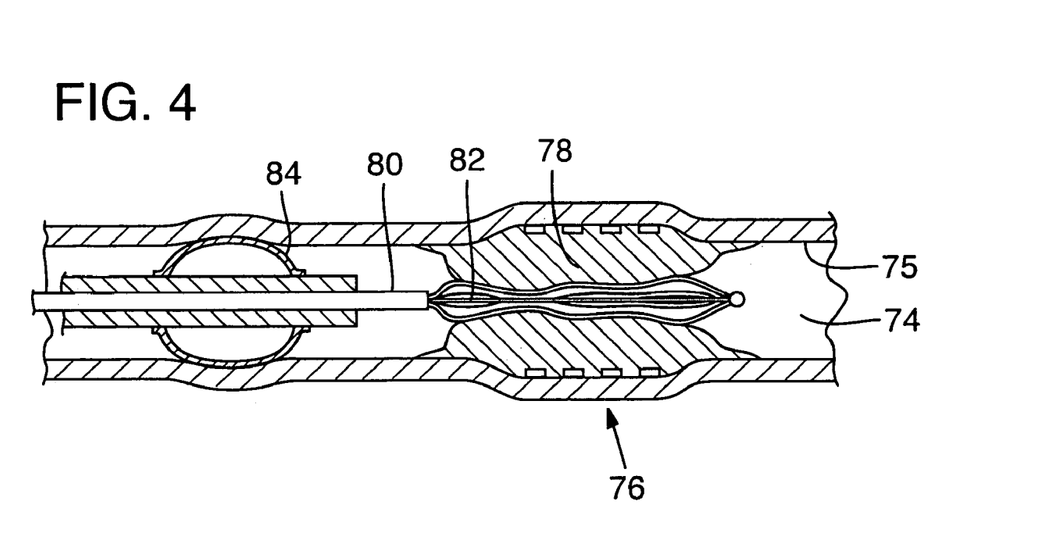
FIG. 4 illustrates a method for increasing the diameter of a blood vessel lumen, or removing an occlusion, using an embodiment of the device disclosed above.

FIG. 4 illustrates the application of substantially conforming RF electrodes to the clinical problem of a stenotic lumen in a hollow organ. Artery 74 has an area of stenosis 76 due to tissue growth and/or inflammation in the inner wall 75 of the artery. The tissue growth 78 impinges on the vascular lumen. To reduce this tissue growth and restore lumen diameter, any of the embodiments of the present disclosure may be deployed in area of stenosis 76. Moreover, a previously noted, stents constructed of RF-conducting material are also suitable for use as distal electrode ends.

For example, FIG. 4 illustrates an electrode embodiment similar to that of FIG. 2A in its deployed position at area of stenosis 76. An electrode 80 with a movable core 82 is adjusted to optimally conform to the irregular shape of the stenosis, and radiofrequency energy is applied. To reduce tendency to thrombosis during application of RF energy, a balloon 84 may be inflated in the vessel to occlude blood flow. Additionally, the entire segment can be isolated by inflation of proximal and distal balloons. See, e.g., Jorgensen et al., Lancet 1:1106–1108 (1989), and U.S. Pat. No. 5,613,949. Blood may be removed from the isolated segment and replaced with a physiologic liquid, such as normal saline. Alternatively, blood may remain in the isolated segment, thereby promoting therapeutic thrombosis and at the same time preventing distal embolization. As lumen diameter increases with successive applications of RF energy, the distal electrode end will continue to conform to inner wall 75 of blood vessel 74, through the memory function of preformed electrodes and/or movement of the movable core relative to the first coaxial section.

The approach outlined in FIG. 4 is suitable for treatment of an arterial stenotic lesion, treatment of an arterial restenotic lesion, treatment of restenosis within or adjacent to a previously placed stent (referred to as in-stent restenosis). It is also suitable for treating tumor ingrowth in stents, for example in growth of a bronchogenic carcinoma into a stented bronchus, or ingrowth of an esophageal carcinoma into an esophageal stent.

As another approach to in-stent restenosis or tumor ingrowth in a stent, energy could be applied directly to the indwelling stent via the electrode. The stent itself may also be used as an electrode at or near the time it is originally placed, for example during the placement procedure, or up to about 1 hour, two hours, 12 hours, 1 day, 2 days, one week, two weeks, one month, two months, or six months following the procedure.

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

We claim:
1. A device, comprising:
a substantially tubular catheter comprising a nonconductive material, the catheter defining a catheter lumen in communication with both a proximal catheter opening and a distal catheter opening;
an electrode having a proximal electrode end and a distal electrode end, the electrode having a non-deployed state inside the catheter lumen in which the catheter substantially surrounds the electrode, and the electrode having a deployed state in which the distal electrode end, after being advanced through the distal catheter opening, substantially conforms to an inner surface of a hollow organ lumen of a subject, the electrode comprising a first section substantially surrounding a second section, wherein the first section and the second section are slidable relative to one another, the electrode further comprising two or more electrode struts attached to the second section at a distal approximation point and to the first section at a proximal approximation point; and
a source of radiofrequency energy electrically connected to the electrode and capable of delivering a therapeutically effective amount of radiofrequency energy to the electrode.

2. The device of claim 1, wherein the distal catheter opening comprises at least one side hole.

3. The device of claim 1, wherein the distal catheter opening comprises at least one end hole.

4. The device of claim 1, wherein the electrode comprises a memory material that assumes a pre-selected shape when not under constraint against assuming the pre-selected shape.

5. The device of claim 1, wherein the electrode comprises an electrically conductive biodegradable material.

6. The device of claim 1, wherein the electrode comprises an outer coating that reduces adherence of the electrode to the inner surface of the organ.

7. The device of claim 1, wherein the distal electrode end is detachable from the proximal electrode end upon delivery of a therapeutically effective amount of energy to the electrode.

8. The device of claim 1, wherein the first section and the second section are coaxial sections.

9. The device of claim 8, wherein the second section comprises a movable core.

10. The device of claim 1, wherein the second section is rotatable relative to the first section.

11. The device of claim 10, wherein the size or shape of the electrode struts is selectively adjustable by rotating the second section relative to the first section.

12. The device of claim 10, wherein the second section can be rotated relative to the first section such that the electrode struts form a dual basket configuration.

13. The device of claim 1, wherein the size or shape of the electrode struts is selectively adjustable by advancing or retracting the second section relative to the first section.

14. The device of claim 1, further comprising a temporary lumen occluder that occludes the lumen proximal to the deployed distal electrode end.

15. The device of claim 14, further comprising a second temporary lumen occluder that occludes the lumen distal to the deployed distal electrode end.

16. The device of claim 1, further comprising a microprocessor that controls energy delivered to the electrode.

17. The device of claim 16, further comprising a thermistor, wherein the microprocessor receives temperature information from the thermistor and, based on this temperature information, adjusts wattage, frequency, duration of energy delivery, or total energy delivered to the electrode.

18. The device of claim 1, wherein the amount of radiofrequency energy delivered to the electrode is capable of substantially occluding the lumen.

19. The device of claim 1, wherein the source of radiofrequency energy is capable of providing up to at least 200 watts of radiofrequency energy to the electrode.

20. The device of claim 1, wherein the source of radiofrequency energy is configured to provide radiofrequency energy to the electrode in a range between about 5 watts and about 200 watts.

21. The device of claim 1, wherein the source of radiofrequency energy is configured to provide radiofrequency energy to the electrode in a range between about 20 watts and about 200 watts.

22. A method of delivering a radiofrequency signal to a wall of a substantially hollow organ having an inner surface, an outer surface, and a lumen substantially bounded by the inner surface, comprising:
    deploying in the lumen the device of claim 1; and
    delivering a therapeutically effective amount of electrical energy to the wall of the organ.

23. The method of claim 22, wherein the method is a method of substantially occluding the lumen.

24. The method of claim 22, wherein the method is a method of controlling bleeding, a method of ablating an arteriovenous malformation, a method of repairing a vascular aneurysm, a method of reducing blood supply to a tumor, or a method of ablating a varix.

25. A method of increasing the diameter of a lumen of a hollow organ within a subject, comprising:
    deploying the device of claim 1 within the lumen of the hollow organ; and
    delivering a therapeutically effective amount of electrical energy to the conductive member such that the lumen diameter is increased.

26. The method of claim 25, wherein the organ is an artery.

27. The method of claim 26, wherein the artery has a stenosis and the method comprises a method of reducing the stenosis.

* * * * *